United States Patent [19]

Nielsen

[11] Patent Number: 5,486,461
[45] Date of Patent: Jan. 23, 1996

[54] CASEIN HYDROLYZATE AND METHOD FOR PRODUCTION OF SUCH CASEIN HYDROLYZATE

[75] Inventor: Per M. Nielsen, Hillerod, Denmark

[73] Assignee: Novo Nordisk A/S, Bagsvaerd, Denmark

[21] Appl. No.: 211,689

[22] PCT Filed: Sep. 9, 1992

[86] PCT No.: PCT/DK92/00326

§ 371 Date: Apr. 13, 1994

§ 102(e) Date: Apr. 13, 1994

[87] PCT Pub. No.: WO93/08702

PCT Pub. Date: May 13, 1993

[30] Foreign Application Priority Data

Nov. 8, 1991 [EP] European Pat. Off. .............. 91610088
Nov. 27, 1991 [EP] European Pat. Off. .............. 91610091
May 27, 1992 [DK] Denmark ..................................... 711/92

[51] Int. Cl.[6] .............................. A23J 3/34; A23J 3/10; A23J 1/20
[52] U.S. Cl. ........................... 435/68.1; 435/42; 435/222; 426/7; 426/18; 426/32; 426/33; 426/41; 426/43; 426/46; 426/556; 426/557; 530/343; 530/407; 530/822; 530/833
[58] Field of Search ............................. 435/42, 68.1, 222; 426/7, 18, 32, 33, 41, 43, 44, 46, 573, 656, 657; 530/343, 407, 822, 833

[56] References Cited

U.S. PATENT DOCUMENTS

| | | | |
|---|---|---|---|
| 4,443,540 | 4/1984 | Chervan et al. | 426/7 |
| 4,452,888 | 6/1984 | Yamazaki et al. | 435/68.1 |
| 4,600,588 | 6/1986 | Ernster | 426/42 |
| 4,636,388 | 1/1987 | Lin et al. | 426/7 |
| 5,141,757 | 8/1992 | Dac et al. | 426/46 |
| 5,314,873 | 5/1994 | Tomita et al. | 435/68.1 |
| 5,356,637 | 10/1994 | Loosen et al. | 426/7 |

FOREIGN PATENT DOCUMENTS

| | | |
|---|---|---|
| 0223560 | 5/1987 | European Pat. Off. . |
| 0274946 | 7/1988 | European Pat. Off. . |
| 0274939 | 7/1988 | European Pat. Off. . |
| 0384303 | 8/1990 | European Pat. Off. . |
| 2541308 | 8/1984 | France . |

*Primary Examiner*—Herbert J. Lilling
*Attorney, Agent, or Firm*—Steve T. Zelson; James J. Harrington

[57] ABSTRACT

The new casein hydrolyzate does not contain any unhydrolyzed casein and is characterized by a defined molecular weight distribution. The method is characterized by being performed by means of three defined proteolytic enzymes and a non-pH star method. The casein hydrolyzate exhibits an optimal balance between DH, free amino acids, bitterness and yield.

13 Claims, 6 Drawing Sheets

CASEIN HYDROLYZATE AND METHOD FOR PRODUCTION OF SUCH CASEIN HYDROLYZATE

The invention comprises a casein hydrolyzate and a method for production of such casein hydrolyzate.

Casein hydrolyzates are mainly used as constituents in baby food, and many different casein hydrolyzates and methods for production of casein hydrolyzates are known. In relation to casein hydrolyzates and methods for production thereof at least four aspects are important in order to generate the best possible result: 1) a high DH (Degree of Hydrolysis), which results in shorter peptides in the product and thus in a low allergenicity, 2) low content of free amino acids, which results in a low osmolality which is preferred when the product is incorporated in a diet, 3) low bitterness, and 4) high yield.

Many methods for production of a casein hydrolyzate with good organoleptic properties can be carried out with a low yield only. Stated more generally, it is difficult to obtain an optimal balance between the above indicated four aspects. Thus, it is the purpose of the invention to indicate a casein hydrolyzate and a method for production of such casein hydrolyzate with optimal properties, i.e. with a high DH, a low content of free amino acids, low bitterness and high yield.

Surprisingly, according to the invention it has been found that a certain combination of specified enzymes and a non-pH-stat hydrolysis provides a process for production of a casein hydrolyzate with an optimal balance between DH, free amino acids, bitterness and yield, The casein hydrolyzate according to the invention does not contain any unhydrolyzed casein, and it is characterized by the fact that the casein hydrolyzate is completely soluble or almost completely soluble in an aqueous medium with a pH value in the pH range of 3.5–7.0, that it is of good organoleptic quality, that it contains peptides in relative amounts corresponding to the following MW distribution (MW is an abbreviation for molecular weight):

|  | weight-% |
| --- | --- |
| MW > 5000 | 0–1 |
| 5000 > MW > 1500 | 15–35 |
| 1500 > MW > 500 | 40–60 |
| 500 > MW | 15–35 | and free amino acids in an amount less than 10% and that the number average molecular weight (Mn) is 400–650.

The MW distribution of peptides in protein hydrolyzates is determined as follows.

1. Principle

The sample is diluted, filtered and injected into a liquid chromatographic system, operating in the Gel Permeation Chromatography (GPC) mode. this separation technique utilizes a liquid flow through a column filled with porous particles, having pores with a well-defined pore diameter. When a solution of peptides, having different molecular sizes passes through the column, the small peptides will be able to flow into the pores while the larger peptides will be excluded from the pores. Thus, the peptides in a solution will be separated according to molecular size (and molecular weight), as the larger peptides will be eluted faster from the column than the smaller peptides. A detector at the column outlet continously measures the effluent. The chromatographic system is calibrated by means of peptides with known molecular weight.

2. Chromatographic Equipment

2.1 HPLC system consisting of
      High Pressure pump, Waters M 510, Flow rate 0.7 ml/min
      Injector, Waters WISP M 710
      Detector, Waters M 440, with wawe lenght extension to 214 nm.
   2.2 GPC column, 3×TSK G 2000 SWXL, 7.8 mm×300 mm, connected in series and operated at ambient temperature.
   2.3 Integration/data processing, Waters 820 MAXIMA SIM chromatography data system with 810/820 GPC option.

3. Reagents

3.1 Phosphate buffer, $NaH_2PO_4.2H_2O$
   3.2 Ammonium chloride, $NH_4Cl$
   3.3 Trifluoroacetic acid (TFA), $CF_3COOH$
   3.4 Acetonitrile, $CH_3CN$
   3.5 Mobile phase:
      0.05M phosphate buffer/0.5M ammonium chloride solution containing 0.1% TFA and 25% acetonitrile 4. Description    4.1 Calibration
      The chromatographic system is calibrated by means of injections of numerous peptide standards with known molecular weight. The molecular weight of each standard is plotted semilogaritmic versus the observed volume of mobile phase needed to elute the peptide from the column. By a least squares calculation, the best fitting 3rd order polynomium is calculated. This curve represents the calibration curve.
   4.2 Analysis
      The sample is diluted/dissolved in mobile phase to approx. 5 mg/ml. The solution is filtered through a 22 µm filter and 20 µl is used for injection into the chromatograph. The detector response versus elution volume is recorded. The recorded curve—the chromatogram—shows the actual MW distribution of the sample. To allow for calculations as to accumulated weight distribution and average molecular weight calculations, the chromatogram is divided into small time (and elution volume) segments—each segment characterized by the elution volume and the area of the chromatogram over the time interval.

5. Calculation
Results are given in terms of weight and number average molecular weights.

$$\overline{M}_w = \frac{\Sigma_i (A_i * M_{w,i})}{\Sigma_i A_i}, \overline{M}_n = \frac{\Sigma_i A_i}{\Sigma_i (A_i/M_{w,i})},$$

where
$\overline{M}_w$: Weight average molecular weight
$\overline{M}_n$: Number average molecular weight
$A_i$: Area of chromatogram for each segment, measured as the accumulated detector response over each time interval.
$M_{w,i}$: The corresponding molecular weight for each segment. The value is calculated by means of the calibration curve, using the average elution volume over the time interval.

A preferred embodiment of the casein hydrolyzate according to the invention is characterized by the fact that the casein hydrolyzate is produced from rennet precipitated casein, and that it contains peptides in relative amounts corresponding to the following MW distribution (MW is an abbreviation for molecular weight):

|  | weight-% |
|---|---|
| MW > 5000 | 0–0.2 |
| MW > 3000 | <5 |
| 5000 > MW > 1500 | 15–35 |
| 1500 > MW > 500 | 40–60 |
| 500 > MW | 15–35 | and free amino acids in an amount less than 10% and that the number average molecular weight (Mn) is 400–650. In this embodiment of the casein hydrolyzate according to the invention the molecular weight of the hydrolyzate is different, as it contains a relatively low amount of long peptides. The absence of high molecular weight peptides reduces the antigenicity. This effect is very important in relation to utilization of the hydrolyzate from rennet casein as an ingredient in mother milk substitutes where low antigenicity is wanted. Also, the digestability will be improved causing less tendency to colic. Thus, the invention also comprises a baby food formulation or mother milk substitute containing this embodiment of the casein hydrolyzate according to the invention.

A preferred embodiment of the casein hydrolyzate according to the invention is characterized by the fact that the casein hydrolyzate is completely soluble in an aqueous medium with a pH value in the pH range of 3.5–7.0. Due to the complete solubility of the casein hydrolyzate it is very well suited as a constituent in dietary food. Also, the invention further comprises a full soluble dietary formulation with good stability at the low pH values indicated and containing this embodiment of the casein hydrolyzate according to the invention as the protein source. Such full soluble dietary formulation based on this embodiment of the casein hydrolyzate according to the invention will prevent coagulation in the stomach which especially is a problem in normal tube feeding products.

Also, the method according to the invention for production of a casein hydrolyzate is characterized by the fact
1) that a casein or caseinate with at least 85% of protein calculated as dry matter is suspended/dissolved in an aqueous medium to a solution with a protein content up to about 20%, preferably up to 10%,
2) that the suspension/solution from step 1) in a one step reaction is proteolytically hydrolyzed to a DH of 15–35%, preferably 22–28% by means of three groups of proteases which are 1) one or more neutral endoproteases from a Bacillus in a concentration of at least 0.005 Anson units/100 g of protein,
2) one or more alkaline endoproteases from a Bacillus in a concentration of at least 0.005 Anson units/100 g of protein, and
3) one or more exoproteases from an Aspergillus in a concentration corresponding to at least 1000 peptidase units/100 g of protein, at a temperature between 45° C. and 60° C. by means of a non-pH-stat method,
3) that the hydrolysis is terminated by inactivation of the enzymes, and
4) that the effluent from step 3) is converted to a dry state.

U.S. Pat. No. 3,761,353 describes a protein hydrolyzate, in relation to which milk protein can be used as a raw material. This protein hydrolyzate is produced with a lower yield than with the method according to the invention. Also, this prior art does not use the same combination of proteolytic enzymes as the method according to the invention.

EP 384 303 describes a method for production of a protein hydrolyzate, which can be a casein hydrolyzate. Even if this casein hydrolyzate exhibits a low bitterness, it is indicated that the DH is of the order of magnitude of 4.4%, whereas the DH in relation to the method according to the invention is 15–35%. Also, the pH is kept constant during the hydrolysis, vide page 6, line 35, whereas the hydrolysis according to the invention is conducted as a non-pH-stat reaction.

EP 223 560 describes a method for production of a protein hydrolyzate, which may be a casein hydrolyzate, by means of a sequential hydrolysis. The hydrolysis in the method according to the invention is a one-step reaction, and also, this prior art does not describe the special combination of proteolytic enzymes which is used in the method according to the invention.

U.S. Pat. No. 4,600,588 describes a milk protein hydrolyzate which is produced by means of another combination of proteolytic enzymes than the combination of the proteolytic enzymes used during the method according to the invention. Also, the prior art milk protein hydrolyzate is used as an emulsifier, whereas the casein hydrolyzate according to the invention is used as a food additive.

It is to be understood that the term "neutral endoprotease from a Bacillus" covers any neutral endoprotease produced by a Bacillus and also proteases identical to this group of enzymes, which have been produced by cloning in other hosts. This interpretation is also to be used in relation to similar terms, e.g. "exoprotease from an Aspergillus".

A typical example of a neutral endoprotease from a Bacillus is Neutrase® from Novo Nordisk A/S, typical examples of alkaline endoproteases from Bacillus are Alcalase®, Esperase®, and Savinase® from Novo Nordisk NS, and a typical example of an exoprotease from Aspergillus is Novozym® 515 from Novo Nordisk NS.

No upper limits for the concentrations of the three enzymes have been indicated, but it is to be understood that the upper limits are derived by the fact that an amount of enzyme which impairs the organoleptic properties of the product or which generates an uneconomical process is unwanted.

In relation to the method according to the invention a carbon treatment can be carried out in order to improve the organoleptic properties. This carbon treatment can be carried out as a separate step or in relation to one of the existing steps. If ultrafiltration is carried out, the carbon may be added in an arbitrary step before the ultrafiltration, and the spent carbon is automatically separated from the reaction mixture in the ultrafiltration step, because the permeate is the wanted product. If no ultrafiltration is carried out, the carbon treatment should be performed as a separate step.

The inactivation of the enzymes (step 3) can be performed by lowering the pH value, preferably to around 4.5, whereby the final product is directly suitable as an additive for a stimulating drink, e.g. orange juice, and/or by increasing the temperature. If the inactivation is carried out by lowering of the pH value, it has been found that a carbon treatment is not necessary in order to improve the organoleptic properties.

A preferred embodiment of the method according to the invention is characterized by the fact that the three groups of proteases in step 2) are 1) one or more of the *Bacillus subtills* neutral endoproteases,
2) one or more of the *Bacillus licheniformis* alkaline endoproteases, and
3) one or more of the *Aspergillus oryzae* exoproteases.

It has been found that the organoleptic properties of the casein hydrolyzate produced according to this embodiment is superior.

A preferred embodiment of the method according to the invention is characterized by the fact that the mixture from step 2) before the termination of the hydrolysis in step 3) or after the termination of the hydrolysis in step 3) is separated on an ultrafiltration/microfiltration unit, the permeate constituting the casein hydrolyzate. In this manner a completely soluble casein hydrolyzate is obtained. As ultrafiltration membranes with a cut-off value below 5000 are very rare and as only 1% of the casein hydrolyzate exhibits a MW above 5000, the cut-off value of the ultrafiltration membrane used in this embodiment is principally of no significance. Higher cut-off values are preferred, though, due to the higher flux.

A preferred embodiment of the method according to the invention is characterized by the fact that the hydrolysis step 2) is carried out for less than 6 hours. In this embodiment it is not necessary to pretreat the raw material in order to generate microbiological stability.

A preferred embodiment of the method according to the invention is characterized by the fact that the inactivation of the enzymes is carried out by treatment with an acid of food quality, preferably hydrochloric acid or citric acid. This embodiment is simple and does not need the use of activated carbon for purification purposes, and also, a product can be produced, which exibits any pH-value between 3.5 and 7.0 when dissolved in water.

A preferred embodiment of the method according to the invention is characterized by the fact that the inactivation of the enzymes is carried out by heat treatment, and that the effluent from step 3) is treated with activated carbon, which is subsequently separated, where, after as step 4) the activated carbon free effluent from step 3) is converted to a dry state. This casein hydrolyzate is especially well suited as an ingredient in baby food.

A preferred embodiment of the method according to the invention is characterized by the fact that step 4) is carried out by means of a combination of hyperfiltration and/or evaporation followed by spray-drying. Hyperfiltration is cheapest for concentration until 20°–30° B. and can also eliminate unwanted salts. Spray-drying provides a final product which is easy to handle.

A preferred embodiment of the method according to the invention is characterized by the fact that acid precipitated casein is used as starting material, and that it is dissolved by means of a base. This embodiment utilizes the cheapest raw material available.

A preferred embodiment of the method according to the invention is characterized by the fact that the acid precipitated casein is dissolved by means of $Ca(OH)_2$. This embodiment provides a final casein hydrolyzate with excellent organoleptic properties.

A preferred embodiment of the method according to the invention is characterized by the fact that rennet precipitated casein is used as starting material, and that it is dissolved with a sodium phosphate or with sodium carbonate. In this embodiment the molecular weight of the hydrolyzate is different, as it contains a relatively low amount of long peptides. This effect is very important in relation to utilization of the hydrolyzate from rennet casein as an ingredient in mother milk substitutes where low antigenicity is wanted. It has been found that the final product exhibits the following molecular weight distribution.

|                     | weight-% |
| ------------------- | -------- |
| MW > 5000           | 0–0.2    |
| MW > 3000           | <5       |
| 5000 > MW > 1500    | 15–35    |
| 1500 > MW > 500     | 40–60    |
| 500 > MW            | 15–35    | and free amino acids in an amount less than 10% and that the number average molecular weight (Mn) is 400–650.

A preferred embodiment of the method-according to the invention is characterized by the fact that rennet precipitated casein is dissolved with a sodium phosphate or with sodium carbonate. In this embodiment a fast hydrolysis and a high yield is obtained.

The invention will be illustrated by the following examples.

EXAMPLE 1

The raw material for the hydrolysis was Ca-caseinate obtained from MD-Foods Denmark (Miprodan 40) containing approx. 87% protein. The caseinate was suspended in deionized water at 50° C. at a concentration of 8% protein. pH, osmolality and Brix was recorded: pH=6.96, osmolality=24 mOsm/kg and °Brix= 7.20. Enzyme was added:

Neutrase® 0.5L in an amount of 2.0% of the protein
Alcalase® 2.4L in an amount of 0.5% of the protein
Novozym® 515 in an amount of 0.8% of the protein The hydrolysis was carried out for 6 hours at 50° C. monitoring the pH, osmolality and Brix. At the end of the, hydrolysis pH was 5.91, osmolality was 222 mOsm/kg, Brix was 12.00° B. and DH was 26.2%. The hydrolysis was terminated by heat treatment for 3 minutes at 85° C.

The separation of the hydrolysis mixture was carried out by means of a PCI ultrafiltration equipment mounted with FP100 membranes (cut off MW=100000). The yield after UF>93%, related to the amount of protein in the raw material. The product was concentrated by means of a PCI nanofiltration equipment mounted with AFC30 membranes. The total yield after this process step was 90.7%. The concentrate was spray-dried.

Figure 1:
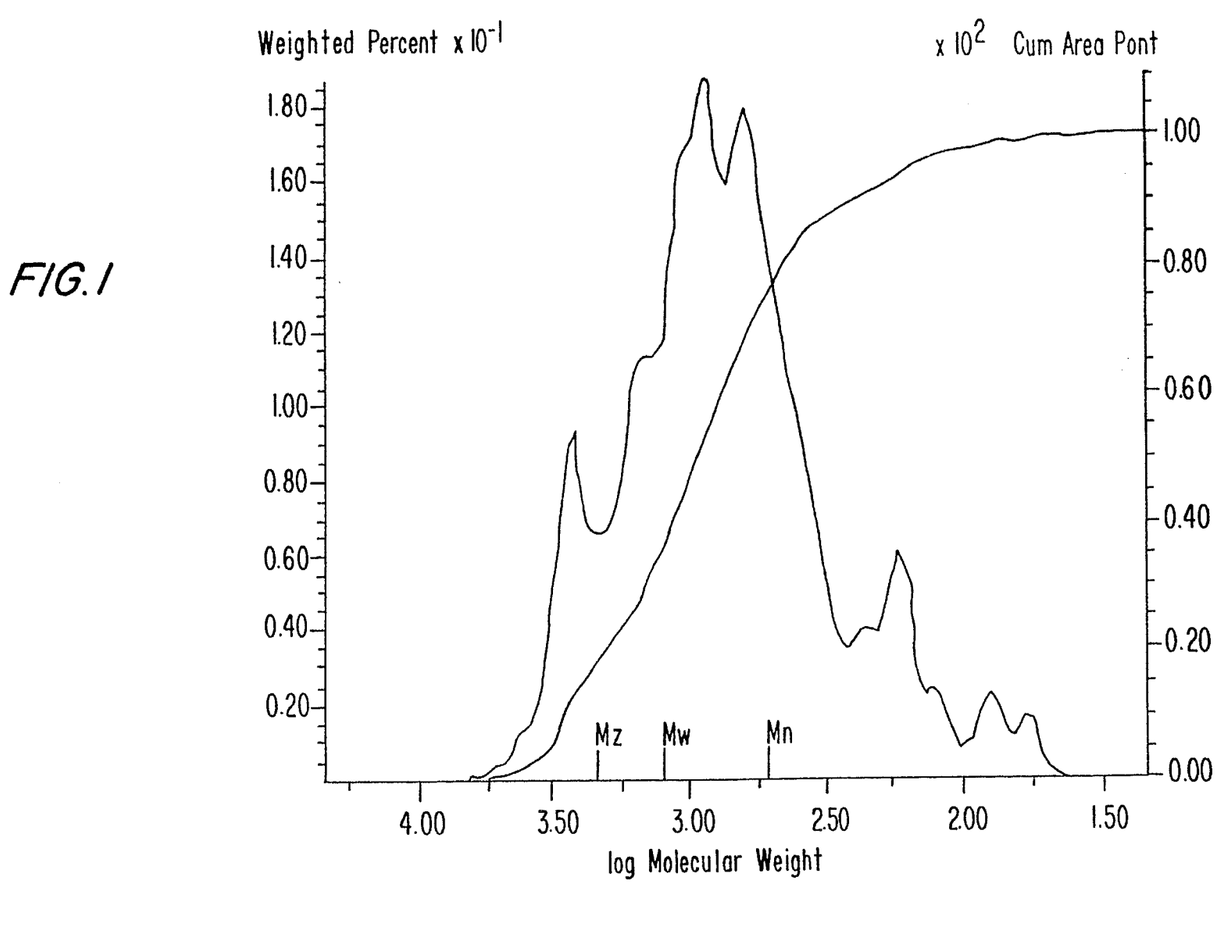
FIG. 1 shows the molecular weight distribution and the accumulated molecular weight distribution of the casein hydrolyzate produced as indicated in Example 1.

The product obtained was a fully soluble powder containing 91% protein in dry matter with a molecular weight distribution according to FIG. 1. Average Mn=516. Free amino acids=7%. The product is fully soluble in the pH range from 3.5 to 7.0. The pH value in a 5% solution of the product was 6.45.

EXAMPLE 2

The raw material for the hydrolysis was Ca-caseinate obtained from MD-Foods Denmark (Miprodan 40) containing approx. 87% protein. The caseinate was suspended in deionized water at 50° C. at a concentration of 8% protein. pH, osmolality and Brix was recorded: pH=6.96, osmolality=24 mOsm/kg and °Brix= 7.20. Enzyme was added:

Neutrase® 0.5L in an amount of 2.0% of the protein
Alcalase® 2.4L in an amount of 0.5% of the protein
Novozym® 515 in an amount of 0.8% of the protein The hydrolysis was carried out for 6 hours at 50° C. monitoring the pH, osmolality and Brix. At the end of the hydrolysis pH was 5.91, osmolality was 222 mOsm/kg, Brix was 12.00° B., and DH was 26.2%. The hydrolysis was terminated by heat treatment for 3 minutes at 85° C. Activated carbon (Picatif 120EW) was added at dosage 4% of °B.

The separation of the hydrolysis mixture was carried out by means of a PCl ultrafiltration equipment mounted with FP100 membranes (cut off MW=100000). The yield after UF>93%, related to the protein in the raw material. The product was concentrated by means of a PCl nanofiltration equipment mounted with AFC30 membranes. The total yield after this process step was 90.7%. The concentrate was spray-dried.

Figure 2:
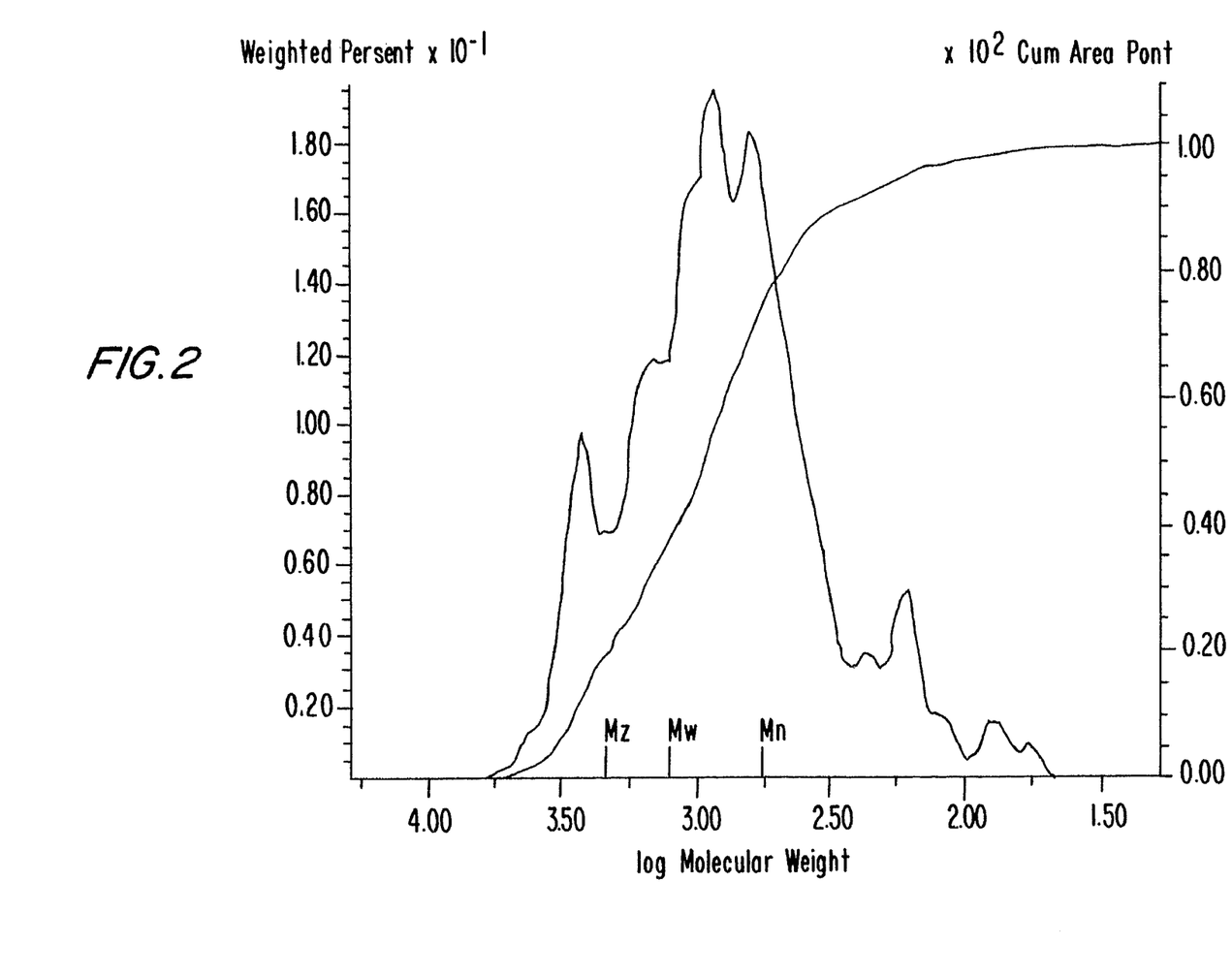
FIG. 2 shows the molecular weight distribution and the accumulated molecular weight distribution of the casein hydrolyzate produced as indicated in example 2.

The product obtained was a fully soluble powder containing 91% protein in dry matter with a molecular weight distribution according to FIG. 2. Average Mn=564. Free amino acids=7%. The taste of this product was described as milder than the taste of the product from Example 1. The product is fully soluble in the pH range from 3.5 to 7.0. The pH in a 5% solution of the product was 6.38.

EXAMPLE 3

The raw material for the hydrolysis was rennet casein obtained from MD-Foods Denmark (Miprodan 26) containing approx. 87% protein. The casein was suspended in deionized water at 75° C. at a concentration of 8% protein. 2% di-sodium-diphosphate and 1% mono-sodium-diphosphate, related to the amount of protein, was added in order to solubilize the casein. Complete solubilization was obtained within 60 minutes. The mixture was cooled to 50° C. pH, osmolality and Brix was recorded: pH=6.95, osmolality=40 mOsm/kg and °Brix= 11.4. Enzyme was added:

Neutrase® 0.5L in an amount of 2.0% of the protein
Alcalase® 2.4L in an amount of 0.5% of the protein
Novozym® 515 in an amount of 0.5% of the protein The hydrolysis was carried out for 6 hours at 50° C. monitoring the pH, osmolality and Brix. At the end of the hydrolysis pH was 6.15, osmolality was 211 mOsm/kg, and Brix was 12.00° B. The hydrolysis was terminated by heat treatment for 3 minutes at 85° C.

The separation of the hydrolysis mixture was carried out by means of a PCl ultrafiltration equipment mounted with FP100 membranes (cut off MW=100000). The yield after UF>80%, related to the amount of protein in the raw material. The product was concentrated by means of a PCl nanofiltration equipment mounted with AFC30 membranes. The total yield after this process step was 77.5%. The concentrate was added activated carbon (Picatif 120EW) at a dosage of 4% of °B., and then it was filtered in a plate filter and spray dried.

Figure 3:
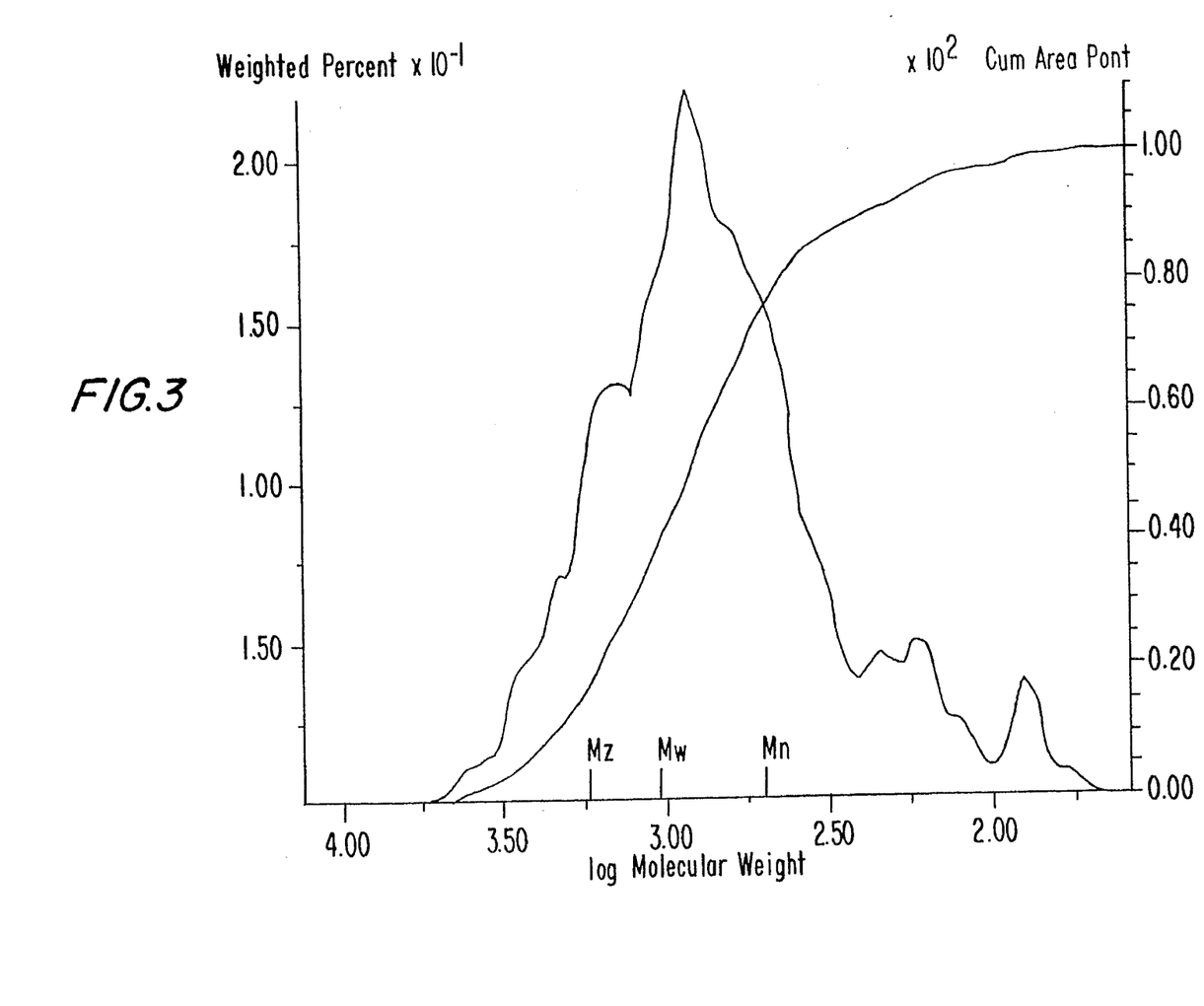
FIG. 3 shows the molecular weight distribution and the accumulated molecular weight distribution of the casein hydrolyzate produced as indicated in example 3.

The product obtained was a fully soluble powder containing 91.3% protein in dry matter with a molecular weight distribution according to FIG. 3. Average Mn=496. Free amino acids=5%. The taste of this product was described as slightly more flavoured compared to the taste of the product from Example 1. The product is fully soluble in the pH range from 3.5 to 7.0. The pH in a 5% solution of the product was 6.50.

EXAMPLE 4

The raw material for the hydrolysis was Na-caseinate obtained from MD-Foods Denmark (Miprodan 30) containing approx. 87% protein. The caseinate was suspended in deionized water at 50° C. at a concentration of 8% protein. Enzyme was added:

Neutrase® 0.5L in an amount of 2.0% of the protein
Alcalase® 2.4L in an amount of 0.5% of the protein
Novozym® 515 in an amount of 0.8% of the protein The hydrolysis was carried out for 6 hours at 50° C. A parallel hydrolysis was carried out under the same circumstances. The only difference was the use of Ca-caseinate (Miprodan 40). Taste evaluation of the mixture after hydrolysis, heat treatment and filtration showed that the hydrolysate made from Ca-caseinate was significantly lower in regard to flavour profile than the hydrolysate made from Na-caseinate.

The product is fully soluble in pH range from 3.5 to 7.0.

EXAMPLE 5

The rate of the hydrolysis was tested comparing rennet casein as raw material in order to investigate impact of solubilization on efficiency of hydrolysis. The raw material for the hydrolysis was rennet casein obtained from MD-Foods Denmark (Miprodan 26) containing approx. 87% protein. The casein was suspended in deionized water at 75° C. at a concentration of 8% protein. 2% di-sodium-diphosphate and 1% mono-sodium-diphosphate, related to the amount of protein, was added in order to solubilize the casein. Complete solubilization was obtained within 60 minutes. The mixture was cooled to 50° C.

Figure 4:
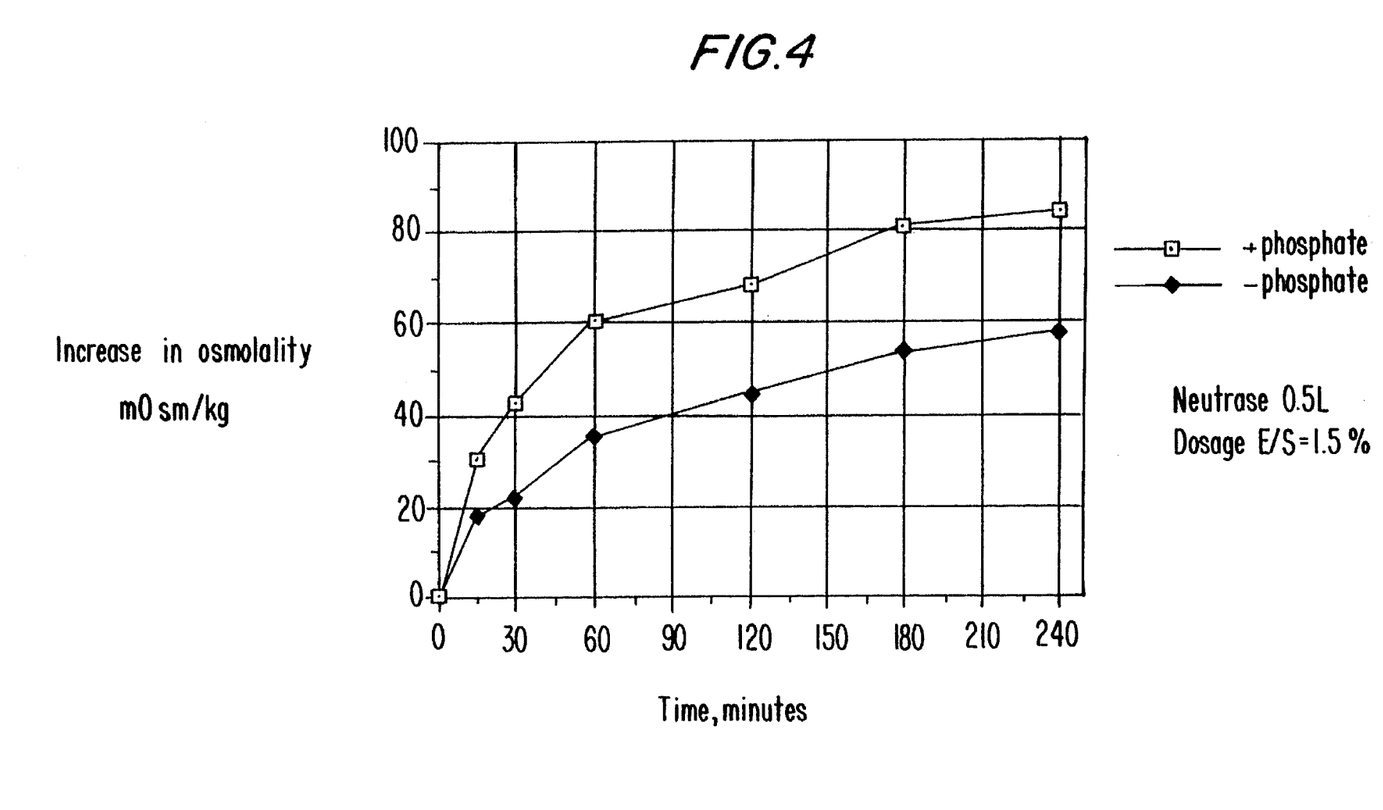
FIG. 4 shows the rate of hydrolysis of rennet casein with and without phosphate, produced as indicated in example 4.

The hydrolysis was carried out for 4 hours monitoring the increase in osmolality. Under the same conditions but without phosphate a parallel hydrolysis was carried out. The rate of hydrolysis was significantly slower as shown on FIG. 4. This also correlates to an increase in yield when rennet casein is solubilized with phosphate before hydrolyzing.

EXAMPLE 6

The raw material for the hydrolysis was Ca-caseinate obtained from MD-Foods Denmark (Miprodan 40) containing approx. 87% protein. The caseinate was suspended in deionized water at 50° C. at a concentration of 8% protein. pH, osmolality and Brix was recorded: pH=6.86, osmolality=25 mOsm/kg and °Brix= 8.40. Enzyme was added:

Neutrase® 0.5L in an amount of 2.0% of the protein
Alcalase® 2.4L in an amount of 0.5% of the protein
Novozym® 515 in an amount of 0.8% of the protein The hydrolysis was carried out for 6 hours at 50° C. monitoring the pH, osmolality and Brix. At the end of the hydrolysis pH was 5.92, osmolality was 212 mOsm/kg, Brix was 11.40° B. and DH was 26.1%. The hydrolysis was terminated by lowering pH to 4.5 by means of 30% HCl followed by heat treatment for 3 minutes at 75° C.

The separation of the hydrolysis mixture was carried out by means of a PCl ultrafiltration equipment mounted with FP100 membranes (cut off MW=100000). The yield after UF>84.7%, related to the amount of protein in the raw material. This was obtained without optimizing diafiltration.

Figure 5:
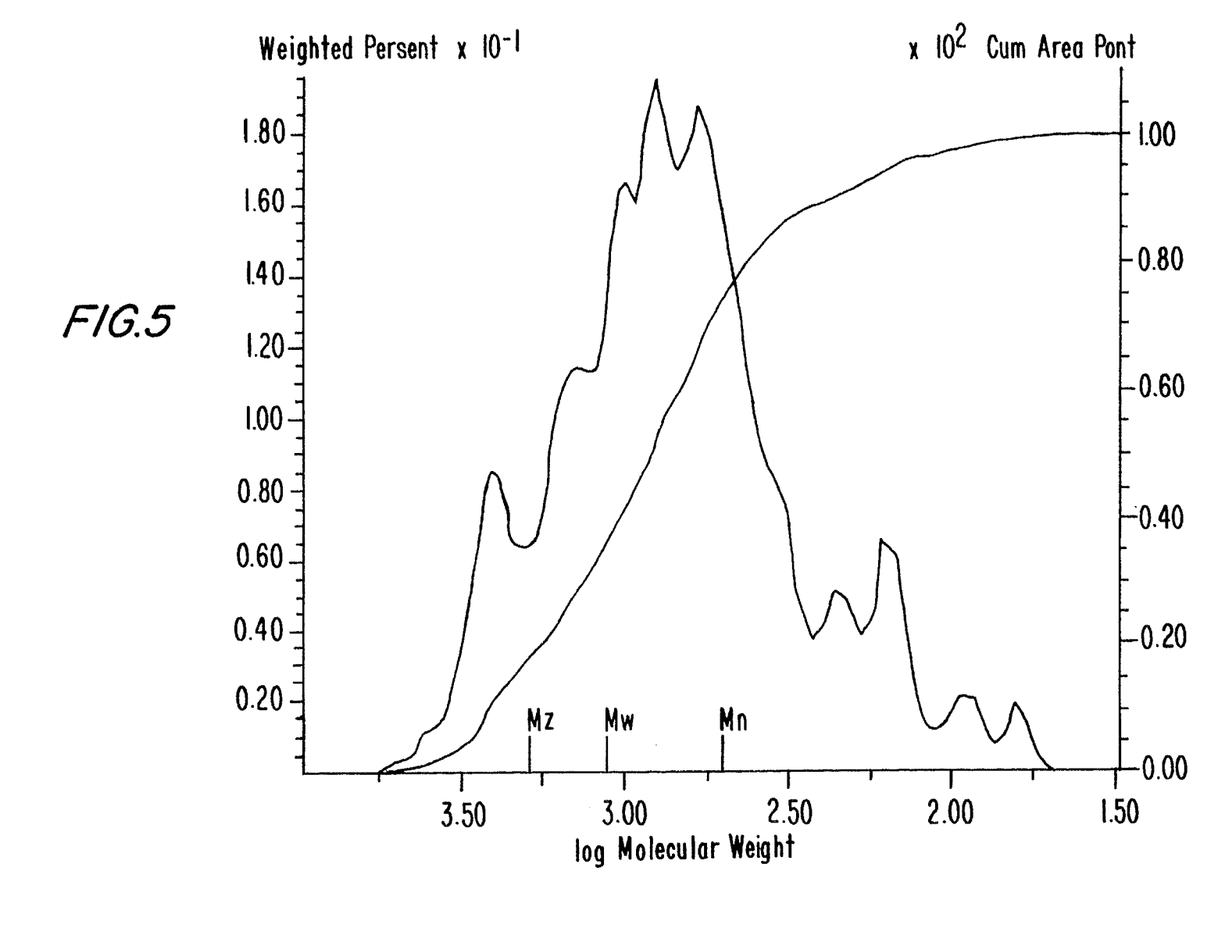
FIG. 5 shows the molecular weight distribution and the accumulated molecular weight distribution of the casein hydrolyzate produced as indicated in example 6.

The product was concentrated by means of a PCI nanofiltration equipment mounted with AFC30 membranes. The total yield after this process step was 79.7%. The concentrate was spray-dried. The product obtained was a fully soluble powder containing 90% protein in dry matter with a molecular weight distribution according to FIG. 5. Average Mn=500. Free amino acids=7%. The pH value of a 5% solution was 4.67.

EXAMPLE 7

The raw material for the hydrolysis was Ca-caseinate obtained from MD-Foods Denmark (Miprodan 40) containing approx. 87% protein. The caseinate was suspended in deionized water at 50° C. at a concentration of 8% protein. pH, osmolality and Brix was recorded: pH=6.86, osmolality=25 mOsm/kg and °Brix= 8.40. Enzyme was added:

Neutrase® 0.5L in an amount of 2.0% of the protein
Alcalase® 2.4L in an amount of 0.5% of the protein
Novozym® 515 in an amount of 0.8% of the protein The hydrolysis was carried out for 6 hours at 50° C. monitoring the pH, osmolality and Brix. At the end of the hydrolysis pH was 5.92, osmolality was 212 mOsm/kg, Brix was 11.40° B. and DH was 26.1%. The hydrolysis was terminated by lowering pH to 4.5 by means of 30% HCl followed by heat treatment for 3 minutes at 75° C.

The separation of the hydrolysis mixture was carried out by means of a PCI ultrafiltration equipment mounted with FP100 membranes (cut off MW=100000). The yield after UF>84.7%, relative to the amount of protein in the is raw material. This was obtained without optimizing diafiltration.

Figure 6:
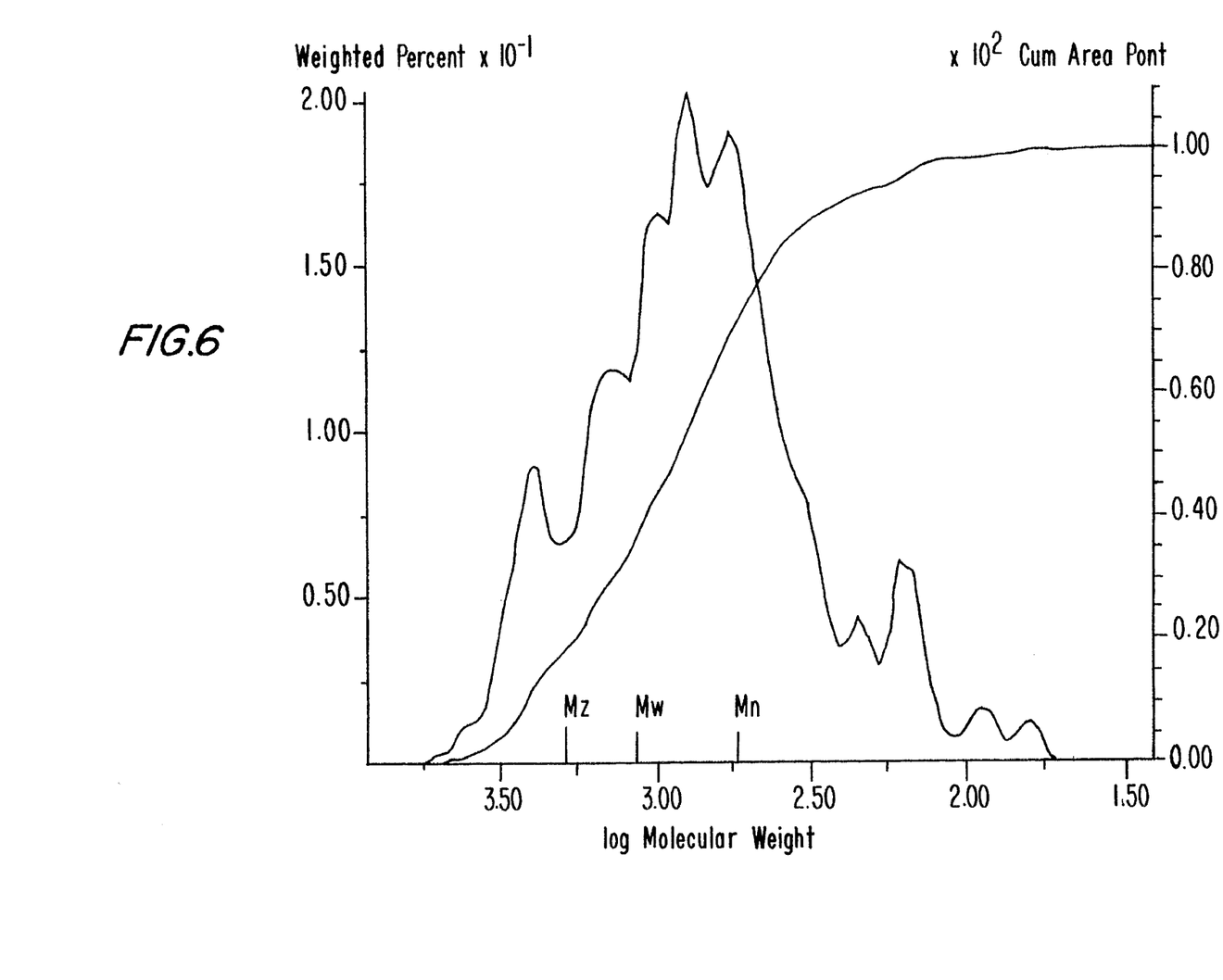
FIG. 6 shows the molecular weight distribution and the accumulated molecular weight distribution of the casein hydrolyzate produced as indicated in example 7.

The product was concentrated by means of a PCI nanofiltration equipment mounted with AFC30 membranes. The total yield after this process step was 79.7%. To the concentrate was added activated carbon (Picatif 120EW) at a dosage of 4% of °B., and then it was filtered in a plate filter and spray-dried. The product obtained was a fully soluble powder containing 89.6% protein in dry matter with a molecular weight distribution according to FIG. 6. Average Mn=541. Free amino acids=7%. The pH value of a 5% solution was 4.64. Taste evaluation (triangel test) showed no significant difference between this product and a product from the previous example, in which no treatment with activated carbon had been carried out.

I claim:

1. A method for production of a casein hydrolyzate, comprising
   a. suspending or dissolving a rennet precipitated or acid precipitated casein or caseinate with at least 85% of protein calculated as dry matter in an aqueous medium to a solution with a protein content up to about 20%,
   b. hydrolyzing the suspension/solution in a one step reaction to a degree of hydrolysis of 15–35% by means of three groups of proteases which are
      i. one or more neutral endoproteases from a Bacillus in a concentration of at least 0.005 Anson units/100 g of protein,
      ii. one or more alkaline endoproteases from a Bacillus in a concentration of at least 0.005 Anson units/100 g of protein, and
      iii. one or more exoproteases from an Aspergillus in a concentration corresponding to at least 1000 peptidase units/100 g of protein, at a temperature between 45° C. and 60° C. without any p.H. adjustment;
   c. terminating the hydrolysis by inactivation of the enzymes to form an effluent; and
   d. converting the effluent to a dry state;

wherein the casein hydrolyzate is completely soluble or at least 99% soluble in an aqueous medium with a pH value in the pH range of 3.5–7.0, is of good organoleptic quality, and contains peptides in relative amounts corresponding to the following MW distribution:

| weight-% | |
| --- | --- |
| MW > 5000 | 0–1 |
| 5000 > MW > 1500 | 15–35 |
| 1500 > MW > 500 | 40–60 |
| 500 > MW | 15–35 | wherein the casein hydrolyzate does not contain any unhydrolyzed casein and contains free amino acids in an amount less than 10% and that the number average molecular weight (Mn) is 400–650.

2. The method according to claim 1, wherein the three groups of proteases in step 2) are
   1) one or more of the *Bacillus subtilis* neutral endoproteases,
   2) one or more of the *Bacillus licheniformis* alkaline endoproteases, and
   3) one or more of the *Aspergillus oryzae* exoproteases.

3. The method according to claim 1, wherein the mixture from step 2) before the termination of the hydrolysis in step 3) or after the termination of the hydrolysis in step 3) is separated on an ultrafiltration/microfiltration unit, the permeate constituting the casein hydrolyzate.

4. The method according to claim 1, wherein the hydrolysis is carried out for less than 6 hours.

5. The method according to claim 1, wherein the enzymes are inactivated by treatment with an acid of food quality.

6. The method according to claim 1, wherein the enzymes are inactivated by heat treatment, and that the effluent from step 3) is treated with activated carbon, which is subsequently separated, whereafter as step 4) the activated carbon free effluent from step 3) is converted to a dry state.

7. The method according to claim 1, wherein step 4) is carried out by means of a combination of hyperfiltration and/or evaporation followed by spray-drying.

8. The method according to claim 1, wherein acid precipitated casein is used as starting material, and that it is dissolved by means of a base.

9. The method according to claim 1, wherein the acid precipitated casein is dissolved by means of $Ca(OH)_2$.

10. The method according to claim 1, wherein rennet precipitated casein is used as starting material, and that the starting material is dissolved with a sodium phosphate or with sodium carbonate.

11. The method according to claim 5, wherein the acid is hydrochloric acid.

12. The method according to claim 5 wherein the acid is citric acid.

13. Casein Hydrolyzate produced according to the method of claim 1.

* * * * *